United States Patent [19]

Fujiwara et al.

[11] Patent Number: 4,670,185

[45] Date of Patent: * Jun. 2, 1987

[54] AQUEOUS VESICLE DISPERSION HAVING SURFACE CHARGE

[75] Inventors: Masami Fujiwara, Kawasaki; Hidenori Fukuda, Minamiashigara; Minako Tanaka, Yokohama, all of Japan

[73] Assignee: Lion Corporation, Tokyo, Japan

[*] Notice: The portion of the term of this patent subsequent to Aug. 20, 2002 has been disclaimed.

[21] Appl. No.: 692,736

[22] Filed: Jan. 18, 1985

Related U.S. Application Data

[63] Continuation-in-part of Ser. No. 514,789, Jul. 18, 1983, Pat. No. 4,536,324.

[30] Foreign Application Priority Data

Jul. 19, 1982 [JP] Japan .................................. 57-125315
Jan. 18, 1984 [JP] Japan ..................................... 59-5640

[51] Int. Cl.$^4$ ............................................. B01J 13/02
[52] U.S. Cl. ..................................... 252/311; 252/312; 264/4.1; 428/402.2
[58] Field of Search ................... 252/311, 312; 264/4.1

[56] References Cited

U.S. PATENT DOCUMENTS

| | | | |
|---|---|---|---|
| 4,217,349 | 8/1980 | Vanlerberghe et al. | 264/4.1 |
| 4,344,968 | 8/1982 | Aoda et al. | 424/365 |
| 4,350,705 | 9/1982 | Hamano et al. | 424/278 |

FOREIGN PATENT DOCUMENTS 1539625 1/1979 United Kingdom .

OTHER PUBLICATIONS

Okalrata et al., Journal of Colloid & Interface Science, vol. 82, No. 2, 1981, pp. 401–417.

Primary Examiner—John F. Terapane
Assistant Examiner—Catherine S. Kilby
Attorney, Agent, or Firm—Armstrong, Nikaido, Marmelstein & Kubovcik

[57] ABSTRACT

An aqueous vesicle dispersion having surface charge comprising (A) 100 parts by weight of at least one ethoxylate selected from the group consisting of polyoxyethylene castor oil ethers and polyoxyethylene hydrogenated castor oil ethers, (B) 3 to 30 parts by weight of at least one sorbitan polyester of long-chain fatty acid, and (C) at least one ionic surfactant. The components (A), (B), and (C) are dispersed in an aqueous medium in such a manner that the components (A) and (B) form vesicle particles in the aqueous medium and the components (C) provides a surface charge on the vesicle particles.

This aqueous vesicle dispersion has an improved dispersion stability and adsorpability of the vesicle particles and can include a hydrophilic or hydrophobic effective component in a state isolated from an aqueous dispersion medium. The aqueous vesicle dispersion can be utilized in the fields of a humectant, a bath salt composition, and a release-controlled topical agent composition.

13 Claims, 4 Drawing Figures

AQUEOUS VESICLE DISPERSION HAVING SURFACE CHARGE

CROSS-REFERENCE TO RELATED APPLICATION

This application is a continuation-in-part of Ser. No. 514,789 filed July 18, 1983 issued on Aug. 20, 1985 as U.S. Pat. No. 4,536,324.

BACKGROUND OF THE INVENTION

1. Field of the Invention

The present invention relates to an aqueous vesicle dispersion utilizing a readily available nonionic surfactant and having a surface charge. More specifically, it relates to an aqueous vesicle dispersion having an improved dispersion stability and adsorbability of the vesicle particles and which is capable of including a hydrophilic or hydrophobic effective or active component in a state isolated from an aqueous dispersion medium.

2. Description of the Related Art

It is known in the art that an amphiphatic substance can form vesicles in water. For example, vesicles such as liposomes based on phospholipids and ufasomes based on unsaturated fatty acids are present in natural substances. Attempts have been made to use these natural vesicles in the fields of cosmetics and pharmaceuticals, since these types of vesicles are stable dispersions and have no safety problems. However, these natural vesicles are not suitable for use in large volume consumption because of their relatively high cost.

Recently, vesicles or niosomes utilizing readily available nonionic surfactants have been found. For example, it has been reported in Japanese Unexamined Patent Publication (Kokai) No. 52-6375 that vesicle dispersions are formed from nonionic surfactants having the general formula:

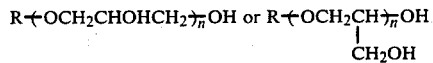

wherein R represents an aliphatic hydrocarbon group having 12 to 30 carbon atoms and n represents an integer of from 1 to 6. It has also been reported in J. Colloid Interface Sci., Vol. 82, No. 2, 401–417 (1981) that vesicles are formed from ethylene oxide addition products of glycerin dialkyl ethers or ethylene oxide addition products of myristic acid stearyl amides. On the other hand, it has been reported in Nippon Kagaku Kaishi, 1981 (11), p 1691–1696 that polyoxyethylene hydrogenated castor oil ethers and polyoxyethylene sorbitol tetraoleate form concentric lamella type liquid crystals.

Vesicles can be considered to be special forms of concentric lamella type liquid crystals. However, vesicles are different from the concentric lamella type liquid crystals in that water or an aqueous solution is contained in a substantial amount in hydrophilic cavities formed in the inside of bimolecular or multiple layer membranes (or films) formed from a surfactant. These cavities are larger than the space between the bimolecular membranes found in regular lamella type liquid crystals.

It is necessary that the surfactant molecules be oriented so as to form lamella bimolecular membranes having a curvature capable of readily forming vesicles. However, although the above-mentioned polyoxyethylene hydrogenated castor oil ethers form concentric lamella type liquid crystals, the polyoxyethylene hydrogenated castor oil ethers cannot form uniform state concentric lamella type liquid crystals and clear vesicle structures since the polyoxyethylene hydrogenated castor oil ethers are mixtures of plural compounds having different ethylene oxide addition mole numbers.

The present inventors have developed a nonionic surfactant type vesicle dispersion which has been found to be acceptable, by official authorities concerned, for use in the fields of foods, drugs, and cosmetics and which can be produced from a readily available surfactant (U.S. Pat. No. 4,536,324 noted above). This nonionic surfactant type vesicle dispersion is formed by adding sorbitan polyesters of long-chain fatty acids to nonionic surfactants, i.e., polyoxyethylene castor oil ethers and/or polyoxyethylene hydrogenated castor oil ethers in a certain ratio to cause the orientation of the nonionic surfactants with a curvature such that vesicles are readily formed. However, the nonionic surfactant type vesicle dispersions thus obtained are still not satisfactory from the viewpoints of dispersion stability and adsorbability of the vesicle particles.

SUMMARY OF THE INVENTION

The object of the present invention is, accordingly, to provide an aqueous vesicle dispersion having an improved dispersion stability and adsorbability and capable of including a hydrophilic or hydrophobic effective or active component therein, in a state isolated from an aqueous dispersion medium.

Other objects and advantages of the present invention will be apparent from the following description.

In accordance with the present invention, there is provided an aqueous vesicle dispersion having a surface charge, the vesicle dispersion comprising (A) 100 parts by weight of at least one ethoxylate selected from the group consisting of polyoxyethylene castor oil ethers and polyoxyethylene hydrogenated castor oil ethers, (B) 3 to 30 parts by weight of at least one sorbitan polyester of long-chain fatty acid, and (C) at least one ionic surfactant. The components (A), (B), and (C) are dispersed in an aqueous medium in such a manner that the components (A) and (B) form vesicle particles in the aqueous medium and the component (C) provides a surface charge on the vesicle particles.

BRIEF DESCRIPTION OF THE DRAWINGS

The present invention will now be illustrated in detail with reference to the accompanying drawings in which.

DESCRIPTION OF THE PREFERRED EMBODIMENTS

Figure 1:
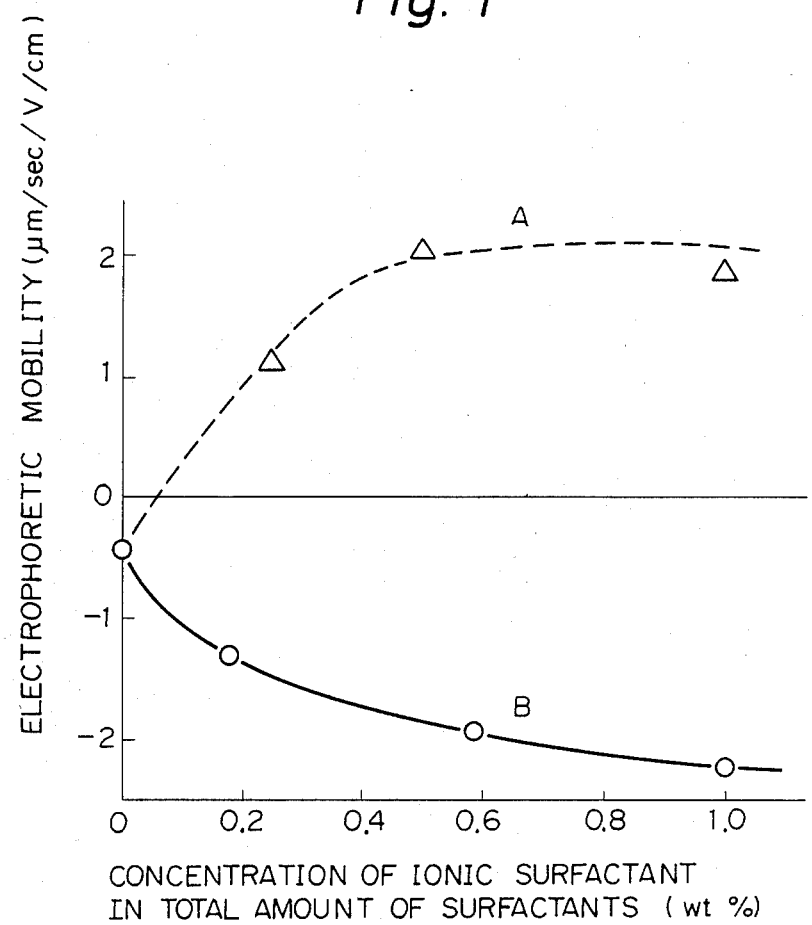
FIG. 1 is a graph illustrating the correlation between the concentration of the ionic surfactant, in the total surfactants, and the electrophoretic mobility of the vesicle particles in the system of aqueous nonionic surfactant vesicle compositions, containing a cationic or anionic surfactant according to the present invention.

The nonionic surfactants forming films of vesicles usable as the component (A) of the vesicle dispersion according to this invention are polyoxyethylene castor oil ethers or polyoxyethylene hydrogenated castor oil ethers. These ethoxylates have the following general formula:

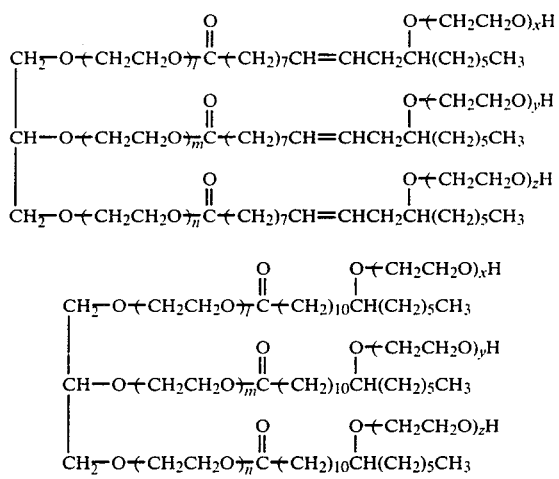

These ethoxylates can be used alone or in any mixture thereof. The average ethylene oxide addition mole number (i.e., $l+m+n+x+y+z$ in the above formula) of these ethoxylates is generally 7 to 20, preferably 8 to 15.

The sorbitan polyesters of long-chain fatty acids usable as the component (B) of the vesicle dispersion according to the present invention are those having long-chain fatty acid residues with 14 to 18 carbon atoms, preferably 16 to 18 carbon atoms. Furthermore, the esterification degree of the sorbitan polyesters of long-chain fatty acids is preferably 2.5 to 3.5, especially 2.8 to 3.2. Typical examples of these sorbitan polyesters of long-chain fatty acids are sorbitan tripalmitate, sorbitan trioleate, and sorbitan tallow fatty acid triesters.

According to the present invention, the component (B) should be used in an amount of 3 to 30 parts by weight, preferably 5 to 25 parts by weight, based on 100 parts by weight of the component (A). When the component (A) is used alone, concentric lamella type liquid crystals are formed but no formation of vesicles is observed by an electron microscope. However, the addition of a small amount of component (B) to component (A) results in the orientation of the surfactants with such a curvature that vesicle particles are readily formed. Thus, the desired vesicles are formed. When the weight ratio of components (A) and (B) are within the above-mentioned range of the present invention, substantially all associates or aggregates formed by the surfactants used form the desired vesicle particles. The above-mentioned preferable range is selected based on the stability of the formed vesicle particles and the retention or keeping properties of various agents (i.e., effective or active components) included or encapusulated in the vesicle particles. An amount of the component (B) of more than 30 parts by weight based on 100 parts by weight of the component (A) results in the destruction of the vesicles (or the formation of the emulsions).

The ionic surfactants usable as the component (C) of the vesicle dispersion according to the present invention are those capable of providing a surface charge on the vesicle particles formed from the components (A) and (B). These ionic surfactants include cationic surfactants and anionic surfactants.

Examples of the cationic surfactants are long-chain alkylamines having 14 to 22 carbon atoms such as palmitylamine, stearylamine, and hydrogenated tallow alkylamines, and the salts thereof; di (long-chain alkyl) amines having 14 to 22 carbon atoms such as dipalmitylamine, distearylamine, and di (hydrogenated tallow alkyl) amine, and the salts thereof; monoalkyl type quaternary ammonium salts having an alkyl group with 14 to 22 carbon atoms such as palmityl trimethyl ammonium salts, stearyl trimethyl ammonium salts, oleyl trimethyl ammonium salts, and hardened tallow alkyl trimethyl ammonium salts; dialkyl type quaternary ammonium salts having two alkyl groups with 14 to 22 carbon atoms such as distearyl dimethyl ammonium salt, and di (hydrogenated tallow alkyl) dimethyl ammonium salts; alkylene oxide addition products of long-chain alkylamines having an alkyl group with 14 to 22 carbon atoms such as bishydroxyethyl stearyl amine, bishydroxyethyl hydrogenated tallow alkyl amine, and polyoxyethylene stearyl amine, and the salts thereof; 2-alkyl substituted imidazolinium salts having an alkyl group with 14 to 22 carbon atoms such as quaternary products of dehydrated cyclized products of stearic acid and hydroxyethyl ethylenediamine; alkyl dimethyl benzyl ammonium salts having an alkyl group with 8 to 12 carbon atoms; alkyl pyridium salts having an alkyl group with 12 to 22 carbon atoms; quaternary ammonium salts having a hydroxyl group, an ether linkage, and an amide linkage; biguanides such as chlorhexidine and the salts thereof; and cationic phospholipids such as dipalmtoyl phosphatydyl ethanolamine. These cationic surfactants may be used alone or in any mixture thereof.

Examples of anionic surfactants are phosphoric mono- and di-esters of long-chain alcohols having 14 to 22 carbon atoms and the salts thereof; phosphoric mono- and di-esters of alkylene oxide addition products of long-chain alcohols having 14 to 22 carbon atoms and the salts thereof; alkylsulfates having 14 to 22 carbon atoms; polyoxyethylene alkyl ether sulfates of alcohols having 14 to 22 carbon atoms; alkane sulfonates having 14 to 22 carbon atoms; olefin sulfonates having 14 to 22 carbon atoms; and anionic phospholipids such as dipalmytoyl phosphatydyl serine. These anionic surfactants may be used alone or in any mixture thereof.

The amount of the component (C) (i.e., the ionic surfactants) incorporated into the aqueous vesicle dispersion should be such that the formation of the vesicle particles from the components (A) and (B) is not adversely affected by the incorporation of the component (C) into the aqueous dispersion. The use of too large an amount of the component (C) tends to form mixed micells, making it almost impossible to confirm the formation of the desired vesicles.

Table 1 shows the correlation between the vesicle formation and the formulation ratio of an ionic surfactant in dispersion systems using various ionic surfactants. These various ionic surfactants are added to a nonionic surfactant mixture of polyoxyethylene (p=10) hydrogenated castor oil ether and sorbitan trioleate (9:1) so that the surfactant concentration in the dispersion system becomes 10% by weight.

TABLE 1

| No. | Ionic surfactant Type of surfactant | Carbon number of alkyl group | % by weight based on the weight of the total surfactants | | | | | | | | | | | | | |
|---|---|---|---|---|---|---|---|---|---|---|---|---|---|---|---|---|
| 1 | | | 0.5 | 1 | 3 | 5 | 7 | 10 | 20 | 30 | 40 | 50 | 60 | 70 | 80 | 90 | 100 |
| 2 | Dialkyl ($C_{14-22}$) dimethyl quaternary ammonium salts | 14-22 | o | o | o | o | o | o | o | o | o | o | o | o | o | o | o |
| 3 | Monoalkyl ($C_{14-22}$) quaternary ammonium salts | 14-22 | o | o | o | o | o | o | | | | | | | | | |
| 4 | Alkyl ($C_{8-12}$) dimethyl benzyl ammonium salts | 8-12 | o | o | o | o | o | o | | | | | | | | | |
| 5 | Alkyl ($C_{12-22}$) pyridinium salts | 12-22 | o | o | o | o | o | o | | | | | | | | | |
| 6 | Quaternary ammonium salts having hydroxyl group, ether linkage, and amide linkage | — | o | o | o | o | o | o | | | | | | | | | |
| 7 | Long-chain alkyl ($C_{14-22}$) ammonium di-long-chain alkyl ($C_{14-22}$) amines and salts thereof | 14-22 | o | o | o | o | o | o | | | | | | | | | |
| 8 | Long-chain alkyl ($C_{14-22}$) amine POE addition products and salts thereof | 14-22 | o | o | o | o | o | o | | | | | | | | | |
| 9 | 2-alkyl ($C_{14-22}$) substituted imidazolinium salts | 14-22 | o | o | o | o | o | o | | | | | | | | | |
| 10 | Biguanide compounds (chlorhexidine) | — | o | o | | | | | | | | | | | | | |
| 11 | Cationic phospholipids | 12-18 | o | o | o | o | o | o | o | o | o | o | | | | | |
| 12 | Anionic phospholipids | 12-18 | o | o | o | o | o | o | o | o | o | o | | | | | |
| 13 | Phosphonic mono- and di-esters of long-chain alcohol ($C_{14-22}$) and salts thereof | 14-22 | o | o | | | | | | | | | | | | | |
| 14 | Phosphone mono- and di-esters of POE addition products of long-chain alcohol($C_{14-22}$) and salts thereof | 14-22 | o | o | | | | | | | | | | | | | |
| 15 | Alkyl ($C_{12-22}$) sulfates | 14-22 | o | o | | | | | | | | | | | | | |
| 16 | Polyoxyethylene alkyl ($C_{14-22}$) ether sulfates | 14-22 | o | o | | | | | | | | | | | | | |
| 17 | Alkane ($C_{14-22}$) sulfonates | 14-22 | o | o | | | | | | | | | | | | | |
| 18 | Olefin ($C_{14-22}$) sulfonates | 14-22 | o | o | | | | | | | | | | | | | |

The formation of vesicles is confirmed by a polarization microscope or an electron microscope and the dispersion system in which the formation of vesicles is confirmed is expressed by the mark "o" in Table 1.

As is clear from the results shown in Table 1, the formulation ratio of the ionic surfactant at which the formation of vesicles is inhibited depends upon the type of the ionic surfactants. For example, dialkyl ($C_{14-22}$) type quaternary ammonium salts capable of forming vesicles themselves can form vesicles with the nonionic surfactants in any formulation ratio. The monoalkyl ($C_{14-22}$) type quaternary ammonium salts, the alkyl ($C_{8-12}$) dimethyl bendyl, the alkyl ($C_{12-22}$) pyridium salts, the long-chain alkyl ($C_{14-22}$) amines and the salts thereof, di(long-chain alkyl ($C_{14-20}$) amines and the salts thereof, the alkylene oxide addition products of long-chain alkyl ($C_{14-22}$) amines and the salts thereof, 2-alkyl ($C_{14-22}$) substituted imidazolinium salts, and the quaternary ammonium salts having a hydroxyl group, an ether linkage, and an amide linkage can form vesicles in a formulation ratio of 10% by weight or less based on the amount of the total surfactants. On the other hand, cationic and anionic phospholipids can form vesicles in a formulation ratio of 50% by weight or less based on the amount of the total surfactants, and the chlorhexidine can form vesicles in a formulation ratio of 5% by weight or less based on the amount of the total surfactants.

Furthermore, the anionic surfactants such as phosphoric mono- and di-esters of alkylene oxidation addition products of long-chain alcohols ($C_{14-22}$) and the salts thereof, alkyl ($C_{14-22}$) sulfates, polyoxyethylene alkyl ($C_{14-22}$) ether sulfates, alkane ($C_{14-22}$) sulfonates, and olefin ($C_{14-22}$) sulfonates can form vesicles in a formulation ratio of 1% by weight or less based on the weight of the total sulfates.

FIG. 1 illustrates one example of the change in the surface charge of non-ionic surfactant vesicle particles caused by the formulation of an ionic surfactant. The change in the surface charge of the vesicle particles is determined by the electrophoretic mobility of the vesicle particles.

FIG. 1 also illustrates the correlation between the concentration of ionic surfactants and the electrophoretic mobility of the vesicle particles in the systems of nonionic surfactant vesicle compositions containing, as an ionic surfactant, benzethonium chloride (i.e., system A) and dipalmitoyl phosphatidyl serine (i.e., system B). The abscissa axis of FIG. 1 is the concentration (%) of the ionic surfactant in the total surfactants and the ordinate axis is the electrophoretic mobility ($\mu$m/sec/v/cm). The concentrations of the nonionic surfactants in the vesicle dispersion were such that the polyoxyethylene ($\bar{p}=10$) hydrogenated castor oil ether was 9% by weight and the sorbitan trioleate was 1% by weight.

As is clear from FIG. 1, when a cationic substance, i.e., benzethonium chloride is used as shown in curve A of FIG. 1, the positive charge on the vesicle particles is increased with the increase in the concentration of the cationic surfactant. Contrary to this, when an anionic substance, i.e., dipalmitoyl phosphatidyl serine, is used as shown in curve B of FIG. 1, the negative charge on the vesicle particles is increased.

The increase in the viscosity of the vesicle dispersion generally corresponds to the formation of associates or aggregates of the vesicle particles, and extensive propagation of the aggregation of the vesicle particles causes phase separation. Accordingly, when the dispersion stability of the vesicle dispersion system is good, the change in the viscosity with the lapse of time is small and phase separation does not occur even during long term storage.

The addition effect of ionic surfactants on the dispersion stability of aqueous nonionic surfactant type vesicle dispersions is shown in, for example, Table 3. That is, aqueous vesicle dispersions having compositions listed in Table 2 were prepared, and these aqueous vesicle dispersions were allowed to stand at a room temperature for a long term. The viscosities of the dispersions were determined and the phase separation conditions were visually observed.

The changes in the viscosities are represented by the relative values obtained by assuming that the viscosities at the preparation are "1.00". The results are shown in Table 3.

The phase separation conditions are visually observed according to the following criteria:
  o: No phase separation observed.
  x: Phase separation observed.

nonionic surfactants, the viscosity increased to approximately two times that of the dispersion immediately after the preparation thereof, when the dispersion was allowed to stand at room temperature for 3 months. Furthermore, clear phase separation occurred after 6 months storage at room temperature.

From the results shown above, it is clear that aqueous vesicle dispersions having good dispersion stability can be prepared by adding a cationic or anionic surfactant to a nonionic surfactant type vesicle dispersion in such an amount that the formation of vesicles is not inhibited.

The aqueous vesicle dispersion according to the present invention can be advantageously used as a carrier of an effective or active component, since various active components can be included or encapsulated in the inside aqueous phase of the vesicle particles or within the membrane of the vesicle particles. For this purpose, the adsorbability of the vesicle particles is an important feature for ensuring the effectiveness of the active components.

The vital surfaces are generally believed to be negatively charged due to the presence of, for example, sialic acid residue at the terminal portions of glycoprotein contained in the cell membranes or vital membranes. Accordingly, it is expected that the utilization probability of vesicle dispersions would be increased when a

TABLE 2

| Composition | | Sample No. 1 | 2 | 3 | 4 | 5 |
|---|---|---|---|---|---|---|
| Non-ionic surfactant | P.O.E. (10) hydrogenated castor oil | ← | ← | ← 9 wt % → | → | → |
| | Sorbitan trioleate | — | ← | ← 1 wt % → | → | → |
| Ionic surfactant | Benzethonium chloride | — | 0.2 wt % | — | — | — |
| | Distearyldimethyl ammonium chloride | — | — | 3.0 wt % | — | — |
| | Sodium POE (3) oleyl ether phosphate | — | — | — | 0.05 wt % | — |
| | Dipalmytoyl phosphatydyl serine | — | — | — | — | 1.0 wt % |
| | Water | balance | balance | balance | balance | balance |

TABLE 3

| Sample No. | | Period allowed to stand (month) | | | | | | | |
|---|---|---|---|---|---|---|---|---|---|
| | | 3 | 6 | 9 | 12 | 15 | 18 | 21 | 24 |
| 1 | Separation condition | o | x | x | x | x | x | x | x |
| | Viscosity | 2 | — | — | — | — | — | — | — |
| 2 | Separation condition | o | o | o | o | o | o | o | o |
| | Viscosity | 1.01 | 1.05 | 1.06 | 1.10 | 1.10 | 1.09 | 1.11 | 1.10 |
| 3 | Separation condition | o | o | o | o | o | o | o | o |
| | Viscosity | 1.00 | 1.01 | 1.01 | 1.02 | 1.03 | 1.03 | 1.02 | 1.03 |
| 4 | Separation condition | o | o | o | o | o | o | o | o |
| | Viscosity | 1.00 | 1.00 | 1.02 | 1.03 | 1.04 | 1.04 | 1.05 | 1.06 |
| 5 | Separation condition | o | o | o | o | o | o | o | o |
| | Viscosity | 1.00 | 1.00 | 1.00 | 1.01 | 1.03 | 1.04 | 1.06 | 1.07 |

As is clearly shown in Table 3, the changes in the viscosities of the vesicle dispersion sample Nos. 2 to 5 according to the present invention were very small, and no phase separation was observed even when the vesicle dipsersions were allowed to stand at room temperature for 24 months. Contrary to this, in the case of the vesicle dispersion sample No. 1 containing only the positive surface charge is given to the vesicle particles. This is because the concentration of active components included in the vesicle particles is increased at the vital surfaces due to the increase in the adsorbability of the vesicle particles to the vital surfaces.

Figure 2:
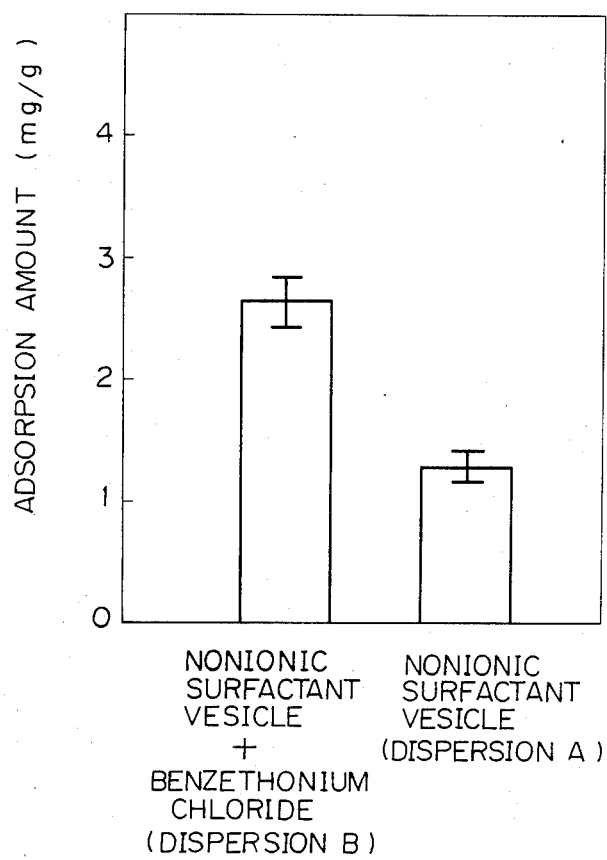
FIG. 2 is a graph illustrating the adsorption amount of vesicles of vital texture in aqueous nonionic surfactant type vesicle dispersions containing, and not containing, a cationic surfactant.

For example, the adsorption amounts of the vesicle particles to vital textures of aqueous vesicle dispersions containing only nonionic surfactants and containing both nonionic surfactants and a cationic surfactant are shown in FIG. 2. That is, FIG. 2 illustrates the comparison of the adsorption amount of the vesicle particles in an aqueous vesicle dispersion containing only nonionic surfactants with the adsorption amount of the vesicle particles in an aqueous vesicle dispersion having a positive surface charge containing nonionic surfactants and benzethonium chloride when the cheek pouch of a Golden hamster is used as the vital surface.

As is clearly shown in FIG. 2, the adsorption amount of the vesicle particles is increased approximately two times by providing a positive surface charge to the vesicle particles.

Figure 3:
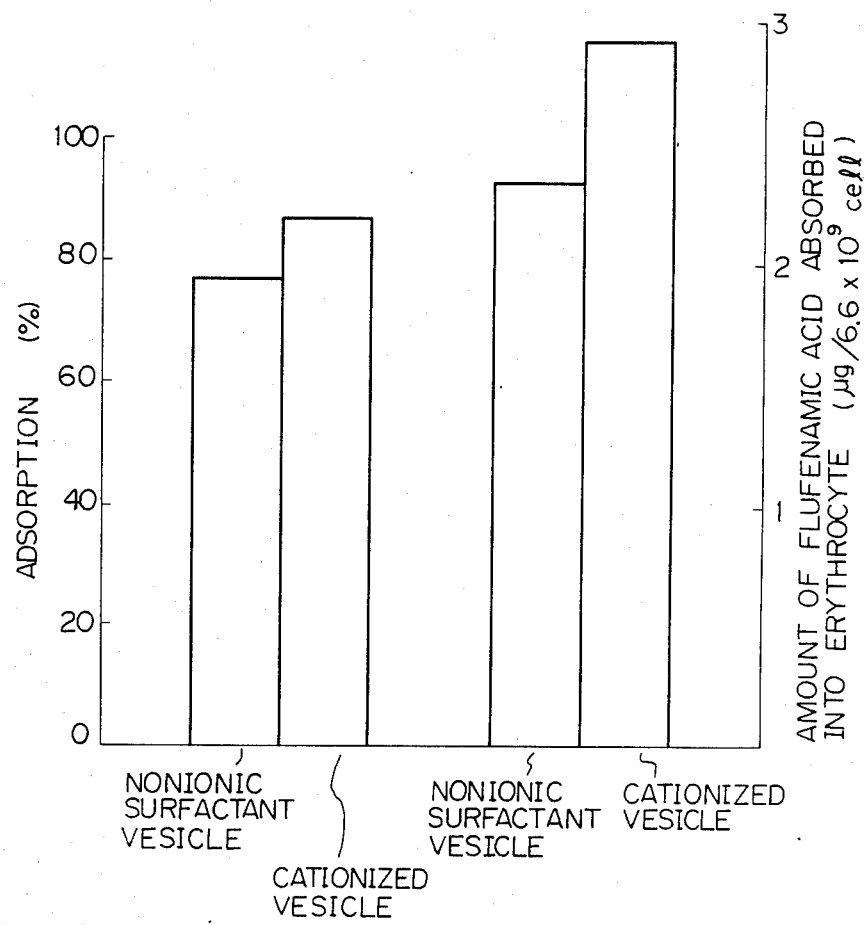
FIG. 3 is a graph illustrating the adsorption amount of vesicles and the absorption amount of an active component to vital texture in aqueous nonionic surfactant type vesicle dispersion containing, and not containing, a cationic surfactant.

The adsorption amounts of vesicle particles and the absorption amounts of active components to a vital texture in a vesicle dispersion containing only nonionic surfactants and a vesicle dispersion containing both nonionic surfactants and a cationic surfactant are shown, for example, in FIG. 3.

FIG. 3 illustrates the comparison of the adsorption amount of vesicle particles to erythrocyte and the absorption amount of flufenamic acid in the presence or absence of distearyl dimethyl ammonium salts in a nonionic surfactant type vesicle dispersion, when flufenamic acid is used as an active component and rabbit erythrocyte is used as a vital texture.

As is clear from the results shown in FIG. 3, both the adsorption amount of the vesicle particles and the absorption amount of the flufenamic acid included in the vesicle particles are increased when a positive surface charge is provided on the vesicle particles by adding distearyl dimethyl ammonium salt to the nonionic surfactant type vesicle dispersion.

Thus, the adsorption amount of the nonionic surfactant type vesicle particles to vital textures can be improved by the addition of cationic surfactants to the nonionic surfactant type vesicle dispersions in an amount such that the formation of vesicles is not inhibited. Furthermore, since these vesicle dispersions contain, as a main constituent, inexpensive which are, nonionic surfactants, harmless to the skin, the vesicle dispersions according to the present invention can be advantageously used as a carrier for increasing the absorption amount of active components to vital textures.

On the other hand, it should be noted that, when objects to be adsorbed or absorbed have a positive charge, similar results or effects can be obtained by including anionic surfactants in the nonionic surfactant type vesicle dispersions to provide the vesicle particles with a negative charge.

The vesicle dispersions according to the present invention can be prepared by, for example, mixing the components (A), (B), and (C) to form a homogeneous phase, followed by mixing with a large amount of water. In this case, the total amount of the components (A), (B), and (C) is preferably 0.1% to 50% by weight, more preferably 5% to 20% by weight, based on the total weight of the dispersion. The resultant vesicle dispersion can be diluted with water or an aqueous solution to any concentration. The mixing methods of the components (A), (B), and (C), and the mixing methods thereof with water, in the preparation of the vesicle dispersion are not specifically limited and may be any conventional mixing methods. For example, conventional mechanical agitation methods and ultrasonic treatments can be used, when the water is mixed with a mixture of the components (A), (B), and (C). When a mixing method of a relatively low shearing force such as mechanical mixing is used, vesicles having a particle diameter of about 1 to 5 $\mu$m are obtained, and vesicles having a particle diameter of about 0.1 to 1 $\mu$m are obtained by the ultrasonic treatment.

The vesicle dispersions according to the present invention can contain hydrophilic and hydrophobic (or lipophilic) agents (i.e., effective components) inside the vesicle particles, depending upon the desired use thereof.

The lipophilic substances optionally contained inside the vesicles of the dispersions of the present invention are, for example, lipophilic agents usable as an effective or active component in pharmaceuticals such as $\beta$-glycyrrhetinic acid, triamcinolone acetomide, and hydrocortisone acetate; oily components or fats and oils such as fatty acid esters, squalane, and liquid paraffin; or other lipophilic substances having a polar group such as chlorohexidine. These substances can be used in any amount as long as the vesicle formation is not impaired.

The hydrophilic substances optionally contained in the inside of the vesicles of the dispersion according to the present invention are, for example, hydrophilic agents usable as an effective or active component in pharmaceuticals such as dipotassium glycyrrhizinate, and chlorhexidine digluconate; humectants having humidity maintaining effects to human skins such as amino acids, pyrrolidone carboxylate, hyaluronic acid, and glycerin. These hydrophilic substances can be used in any amount, as for lipophilic substances, as long as the vesicle formation is not impaired.

The incorporation of the above-mentioned lipophilic or hydrophilic substances can be effected by, for example, mixing the components (A), (B), and (C) and the above-mentioned lipophilic or hydrophilic substances together to form a homogeneous phase, followed by mixing with a large amount of water.

The vesicle dispersions according to the present invention can contain various kinds of active components in the water phase inside the vesicles or in the membrane of the vesicles and, therefore, the vesicle dispersion can be used as a carrier for including or encapusulating the effective components. Furthermore, the membrane component forming the vesicles is a surfactant having a strong lipophilic part and, therefore, the vesicles themselves can act as an oily component of cosmetics. Consequently, the vesicle dispersions according to the present invention can be desirably used in pharmaceuticals and emulsion type cosmetics such as creams and milky lotions. When the vesicle dispersions according to the present invention are used in the above-mentioned application fields, the necessary components can be added to the vesicle dispersion during the preparation step thereof and the resultant vesicles dispersions can be directly used. Alternatively, the vesicle dispersions thus obtained can be added to an aqueous solution or dispersion containing the necessary components or can be simply diluted with water.

The vesicle dispersion according to the present invention has an extremely high practical utility, since the resultant dispersions are stable for a long term, are available at a low cost, and are harmless to the skin, and since readily available surfactants are used for the formation of the vesicle dispersions.

Furthermore, the formation of vesicles can be basically confirmed by observation (e.g., visual observation and micrographs) of an electron microscope.

The aqueous vesicle dispersions having a surface charge according to the present invention per se can be utilized as a humectant since the vesicles per se have a emollient factor (i.e., an action which prevents the drying of horney layers on the skin surface). The humectants according to the present invention can further contain, in addition to the aqueous vesicle dispersions, moisturizing components. Examples of the moisturizing component are organic acids and the derivatives thereof such as lactic acid, pyrrolidone carboxylic acid, tartaric acid, citric acid, amino acids (e.g., glycine and histidine), and metallic salts (e.g., Na and K salts) of the above-mentioned organic acids, the esters and other derivatives of pyrrolidone carboxylic acid, the molecular compounds of allantoin, and the metallic salts of pyrrolidone carboxylic acid; polyhydric alcohols and the derivatives thereof such as glycerol, 1,3-butylene glycol, propylene glycol, polyethylene glycol, sorbitol, glucose, fructose, ribose, deoxyribose, lactose, mannose, and glucose derivatives (e.g., methylglucoside); nitrogen-containing compounds such as urea, collagen hydrolysates, peptide, lanolin-protein complexes, glucosamine, creatinine, and mucopolysaccharides (e.g., hyaluronic acid and chondroitin sulfuric acid); and aloe extracts (e.g., products obtained by effecting an activated carbon treatment or a heat-extracting treatment to sap such as *Aloe vera, Aloe arborscens, Aloe saponaria*). These moisturizing components can be used alone or in any mixture thereof, preferably, in an amount of 0.1% to 10% by weight, based on the total weight of the humectants.

The aqueous vesicle dispersions having a positive surface charge according to the present invention can be used as bath salt compositions. The bath salt compositions are used for affording afterbath effects to the skin such as heat-retention, smoothness, refreshed feeling, and moistness. The bath salt composition according to the present invention preferably comprises: (i) an aqueous vesicle composition composed of, dispersed in an aqueous medium, (A) 100 parts by weight of at least one ethoxylate selected from the group consisting of polyoxyethylene castor oil ethers and polyoxyethylene hydrogenated castor oil ethers and (B) 3 to 30 parts by weight of at least one sorbitan polyester of long-chain fatty acid; and (ii) (C) 30% by weight or less, based on the amount of the total surfactants, of at least one cationic surfactant mentioned above, and (D) 0.1% to 50% by weight, based on the total weight of the above-mentioned components (A), (B), (C), and (D), of at least one organic heat-retention agent.

Examples of the organic heat-retention agents are essential oils such as cinnamomum oil, peppermint oil, mint oil, hinoki oil, turpentine oil, and pine oil; and plant extracts such as extracts of various plants, i.e., extracted liquids obtained by extraction from plants with water or organic solvents such as methanol, ethanol, glycerol, and other alcohols, hexane, acetone, and dichloromethane or the residues obtained by distilling off the extracting solvents. Examples of such plants are Japanese Angelica Root, Citrus Unshiu Peel, Scutellaria Root, iris, Rosemary, mugwort, Peony Root, Eucalyptus, Coix Seed, and ginger. These essential oils and plant extracts may be used alone or in any mixture thereof.

The aqueous vesicle dispersions having a positive surface charge according to the present invention can be used as release-controlled topical agent compositions. The release-controlled topical agent compositions according to the present invention comprise: (i) 0.005% to 0.5% by weight of at least one cationic surfactant mentioned above; (ii) an effective amount (e.g., 0.001% to 60% by weight) of at least one active component; and (iii) an aqueous vesicle dispersion composed of, (A) 100 parts by weight of at least one ethoxylate selected from the group consisting of polyoxyethylene castor oil ethers and polyoxyethylene hydrogenated caster oil ethers and (B) 3 to 30 parts by weight of at least one sorbitan polyester of long-chain fatty acid, dispersed in an aqueous medium. The amount of the components (A) and (B) is within the range of 0.1% to 30% by weight based on the weight of the aqueous vesicle dispersion.

Examples of the active components usable in the present topical or local agent compositions according to the present invention are as follows:

(1) Bactericide and disinfectant

Benzalkonium chloride, benzethonium chloride, cetylpyridinium chloride, chlorhexidine, chlorhexidine gluconate, palmityl trimethyl ammonium chloride, thymol, decanium chloride, thimerosal, mercurochrome, silverprotein, chloramine, sodium hypochlorite, potassium chlorite, iodine, sodium iodide, iodine tincture, povidone iodine, iodoform, oxidol, potassium permanganate, sodium perborate, ethanol, isopropanol, phenol, cresol, bithionol, acrinol, methylrosaniline chloride, nitrofurazone, resorcinol, domifen bromide, TEGO-51, chlorobutanol, salicylic acid, hexachlorophene, benzyl alcohol, benzoic acid, creosote, acriflavine, phenyl salicylate, sodium N-lauroyl sarcosinate, berberine chloride, and berberine sulfate.

(2) Sulfa drug

Homosulfamine, sulfamine, sulfisoxazol, sodium sulfisoxazol, sulfamethoxazol, sulfisomidine, sulfadiazine, sodium sulfisomidine, and sodium sulfamethoxazol.

(3) Local anesthetic

Dibucaine hydrochloride, procaine hydrochloride, hexothiocaine hydrochloride, benzyl alcohol, ethyl aminobenzoate, benzocaine, tetracaine hydrochloride, lidocaine, lidocaine hydrochloride, mepivacaine hydrochloride, cocaine hydrochloride, guatacaine hydrochloride, butanicaine hydrochloride oxibutanicaine hydrochloride, meprylbutanicaine hydrochloride, piperocaine hydrochloride, chlorobutanol, and meprylcaine hydrochloride.

(4) Antihemorrhagic drug and vasoconstrictor

Naphazoline nitrate, phenylephrine hydrochloride, naphazoline hydrochloride, tetrahydrozoline hydrochloride, oximethazoline hydrochloride, tramazoline hydrochloride, epinephrine, thrombin, calcium gluconate, calcium chloride, calcium asparate, cyclonamine, ferric chloride, ε-aminocaproic acid, tranexamic acid, carbazochrome, carbazochrome sodium sulfonate, adrenochrome monoaminoguanidine methanesulfonate, rutin, hesperidin, methyl ephedrine, methyl ephedrine hydrochloride, hinokitiol, and epidihydrocholesterin.

(5) Antihistaminic and antiallergic drug

Crotamiton, thonzylamine hydrochloride, diphenhydramine hydrochloride, methdilazine hydrochloride, promethazine hydrochloride, diphenhydramine salicylate, diphenhydramine tannate, chlorophenylamine, chlorophenylamine maleate, isothipenzyl hydrochloride, diphenhydramine, isoproheptine hydrochloride, and diphenyl imidazole.

(6) Antitussive and asthma treatment drug

Methylephedrine hydrochloride, ephedrine hydrochloride, noscapine, codeine phosphate, dextromethorphar, oxoramine, tipepidine, methylephedrine, isoprotenol, chlorprenaline, salbutanol, papaverine, aminophylline, apomorphine, emetine, pilocarpine, turpentine oil, eucalyptus oil, and guaiacol.

(7) Vitamins

Lecithin, nicotinic acid amide, ergocalciferol, calciferol, tocopherol, tocopherol acetate, ichthammol, lecithinol acetate, lecithinol palmitate, pantothenyl ethyl ether, riboflavin lactate, thiamine oil, pyridoxine dicaprylate, ascorbic acid, piridoxine hydrochloride, riboflavin, calcium pantotenate, cyanocobalamine, vitamin A, pantothenol, water-soluble vitamin A, dexpantothenol, and flavin adenine dinucleotide (8) Hormone Estradiol benzoate, hexestrol, methyltestosterone, and testosterone propionate, (9) Cytoactivator Azulene, water-soluble azlene, chlorophylline, sodium chondroitin sulfate, urea, aminoethyl sulfonate, allantoin, potassium L-aspartate, magnesium L-aspartate, chlorophyll, sodium copper chlorophylline, sodium gualenate, and potassium guaiacolsulfonate.

(10) Antibiotics

Chloramphenicol, demethylchlorotetracycline hydrochloride, fradiomycin, sulfate, trichomycin, clotrimazole, baeitracin, colistin sulfate, colistin sodium methanesulfonate, and erythromycin lactobionate.

(11) Non-steroid type antiphlogistic

Glycyrrhetic acid, flufenamic acid, mefenamic acid, indomethacin, methyl salicylate, glycol salicylate, dipotassium glycyrrhizinate, and phenylbutazone.

(12) Steroid drug

Hydrocortisone, dexamethasone, betamethasone, prednisolone, methylprednisolone, hydrocortisone acetate, dexamethasone acetate, betamethasone valerate, triamcinolone acetonide, and fluorometholone.

(13) Crude drug and Kanpo medicine

Rose mary extract, Corydalistuber, Glycyrrhiza extract, Cimicituga Rhizome extract, Ginseng extract, Platycodon Root extract German Chemomile tincture, Ephedraherb extract, Ipecac extract, Coptis Rhizoml extract, Platycodon Root extract, Safflower extract, aloe extract, Rhatany Root tincture, Clove oil, Cinnamon oil, Phellodondron extract, Japanese angelica root extract, Peony root extract, Capsicum extract, Capsicum tincture, Arnica extract, Belladonna extract, Scopolia extract, hinokitiol, Gardenia fruit, Atractylodes Lancea tincture, Lithospermum Root extract, Eucalyptus oil, Nutmeg extract, Rhubarb extract.

(14) Endobiotic cutaneous disease remedy agent

Dimazole dihydrochloride, thiamthol, nystatin, haloprogin, undecylanic acid, phenyliodide undecynoate, bisdequalonium diacetate, tolnaftate, griseofulvin, pyrrolnitrin, and siccanin.

(15) Enzyme preparation

Dextranase, lyzozyme chloride, amylase, lipase, and protease,

(16) Local stimulant

Camphor, d-borneol, caffein, menthol, tannic acid, and ichthammol.

(17) Peptic ulcer remedy agent

Methylmethionine sulfonium chloride, pipethanate hydrochloride, L-glutamine, isopropamide iodide, histidine hydrochloride, oxethazaine, sulpiride, urogastron, sucralfate, aldioxa, gefarnate, glycyrrhizin, sodium gualenate chlorbenzoxamine hydrochloride, senthienate bromide, and glycopyrronium bromide.

(18) Parasympathetic agent

Neostigmin methylsulfate.

(19) Hair growth agent

Capronium chloride

These pharmaceutically active agents may be used alone or in any mixture thereof. Furthermore, of the above-mentioned cationic surfactants, active components such as benzalconium chloride, benzethonium chloride, and cetylpyridinium can be used as a liniment composition without incorporating other active agents into the composition.

EXAMPLES

The present invention now will be further illustrated by, but is by no means limited to, the following examples, in which all percentages are by weight unless otherwise specified.

EXAMPLE 1

A 9 g amount of polyoxyethylene hydrogenated castor oil ether having an average ethylene oxide addition mole number ($\bar{p}$) of 10 (i.e., component A), 1 g of sorbitan trioleate (i.e., component B), and 2 g of distearyl dimethyl ammonium chloride were weighed in a 100 ml beaker and were thoroughly mixed together at room temperature in the beaker. Then, 88 g of water was added to the resultant mixture and was thoroughly mixed to form a uniform translucent white milky vesicle dispersion having flowability or fluidity.

The formation of the vesicles was visually confirmed by an electron microscope. The particle diameters of the vesicles were within the range of 0.1 to 5 μm. It was confirmed by an electrophoretic test that the resultant vesicle particles had a positive surface charge. Furthermore, the resultant aqueous vesicle dispersion was extremely stable when the dispersion was allowed to stand at a room temperature for more than 24 months.

EXAMPLE 2

A vesicle dispersion was prepared in the same manner as for Example 1, except that polyoxyethylene castor oil ether ($\bar{p}=10$) was used in lieu of component A of Example 1.

The visual appearance, surface charge, stability, and particle diameter of the resultant vesicle dispersion were the same as those of the vesicle dispersion of Example 1.

EXAMPLE 3

A 9 g amount of component A of Example 1, 1 g of component B of Example 1, and 0.2 g of benzethonium chloride (i.e., component C) were thoroughly mixed in a 100 ml beaker. Then, 89.9 g of water was added to the mixture and the resultant mixture was thoroughly mixed together at room temperature with a magnetic stirrer to obtain a homogeneous mixture. Thus, a translucent milky vesicle dispersion having fluidity was obtained.

The formation of the vesicles was visually confirmed by an electron microscope. The particle diameters of the vesicle particles were within the range of 0.1 to 5 μm. Furthermore, the resultant vesicle particles had a positive surface charge when confirmed by an electrophoretic test and the resultant aqueous vesicle dispersion was extremely stable when the dispersion was allowed to stand at a room temperature for more than 24 months.

EXAMPLE 4

A 9 g amount of component A of Example 1, 1 g of component B of Example 1, and 0.2 g of benzalkonium chloride (i.e., component C) were thoroughly mixed in a 100 ml beaker. Then, 89.8 g of water was added to the mixture and the resultant mixture was thoroughly mixed together at room temperature with a magnetic stirrer to obtain a homogeneous mixture. Thus, a translucent milky vesicle dispersion having fluidity was obtained.

The formation of the vesicles was visually confirmed by an electron microscope. The particle diameters of the vesicle particles were within the range of 0.1 to 5 μm. Furthermore, the resultant vesicle particles had a positive surface charge when confirmed by an electrophoretic test and the resultant aqueous vesicle dispersion was extremely stable when the dispersion was allowed to stand at a room temperature for more than 24 months.

EXAMPLE 5

A 9 g amount of component A of Example 1, 1 g of component B, and 0.2 g of chlorhexidine hydrochloride (i.e., component C) were thoroughly mixed in a 100 ml beaker. Then, 89.8 g of water was added to the mixture and the mixture was thoroughly mixed together with a magnetic stirrer to form a homogeneous mixture. Thus, a translucent milky vesicle dispersion having fluidity was obtained.

The formation of the vesicles was visually confirmed by an electron microscope. The particle diameters of the vesicle particles were within the range of 0.1 to 5 $\mu$m. Furthermore, the resultant vesicle particles had a positive surface charge when confirmed by an electrophoretic test and the resultant aqueous vesicle dispersion was extremely stable when the dispersion was allowed to stand at a room temperature for more than 24 months.

EXAMPLE 6

A 9 g amount of component A of Example 1, 1 g of component B of Example 1, and 0.1 g of sodium lauryl sulfate (i.e., component C) were thoroughly mixed in a 100 ml beaker. To the resultant mixture, 89.9 g of water was then added and the mixture was mixed together at room temperature with a magnetic stirrer to obtain a homogeneous mixture. Thus, a translucent milky vesicle dispersion having fluidity was obtained.

The formation of the vesicle was visually confirmed by an electron microscope. The particle diameters of the vesicle particles were within 0.1 to 5 $\mu$m. Furthermore, the resultant vesicle particles had a positive surface charge when confirmed by an electrophoretic test and the resultant aqueous vesicle dispersion was extremely stable when the dispersion was allowed to stand at a room temperature for more than 24 months.

EXAMPLE 7

A 9 g amount of component A of Example 1, 1 g of component B of Example 1, and 0.2 g of benzethonium chloride (i.e., component C) were thoroughly mixed in a 100 ml beaker and, then, 90 g of water was added to obtain a homogeneous mixture. The resultant vesicle dispersion was completely subjected to ultrasonic irradiation.

The finally obtained mixture was translucent and contained vesicles having a particle diameter of 0.1 to 1 $\mu$m. Furthermore the resultant vesicle particles had a positive surface charge which was confirmed by an electrophoretic test and the resultant aqueous vesicle dispersion was extremely stable when the dispersion was allowed to stand at a room temperature for 24 months.

EXAMPLE 8

An aqueous vesicle dispersion A comprising polyoxyethylene ($\bar{p}=10$) hydrogenated castor oil ether and sorbitan trioleate (9:1 by weight) and having a nonionic surfactant concentration of 0.1% was prepared in the same manner as in Example 1. An aqueous vesicle dispersion B was prepared by adding 0.2%, based on the weight of the nonionic surfactants, of benzethonium chloride to the above-prepared aqueous vesicle dispersion A.

The adsorbability of these vesicle dispersions A and B were evaluated by using, as a vital surface, the cheek pouch of a Golden hamster. That is, 0.3 to 0.5 g of the cheek pouch was adsorbed to the aqueous vesicle dispersion at a temperature of 35° C. and at a bath ratio of about 10 times for an adsorption reaction period of 1 hour. The results are shown in FIG. 2. In FIG. 2, the estimation was carried out on the basis of 95% confidence limits.

As is clearly shown in FIG. 2, the adsorbability of the vesicle dispersion B containing benzethonium chloride was approximately twice that of the vesicle dispersion not containing benzethonium chloride. It is believed that this occurs because the positive surface charge is charged onto the surfaces of the vesicle particles of the dispersion B due to the inclusion of benzothonium chloride therein.

EXAMPLE 9

An aqueous vesicle dispersion C comprising polyoxyethylene ($\bar{p}=10$) hydrogenated castor oil ether and sorbitan trioleate (9:1) and having a nonionic surfactant concentration of 1.6% was prepared in the same manner as in Example 1. An aqueous vesicle dispersion D was prepared by adding 20%, based on the weight of the nonionic surfactants, of distearyl dimethyl ammonium chloride to the above-prepared aqueous vesicle dispersion C.

A 4 ml amount of physiologic saline was added to 1 ml of the aqueous vesicle dispersion obtained above. After flufenamic acid, as an active component, and $6.6 \times 10^9$ cells of rabbit erythrocyte as a cell were added to the mixture of physiologic saline and the vesicle dispersion, the resultant mixture was incubated at a temperature of 40° C. for 1 hour. The amount of the vesicles adsorbed into the erythrocyte cells was determined. The results are shown in FIG. 3.

Then, the mixture was washed five times with a 2% HCO-60 (i.e., polyoxyethylene ($\bar{p}=60$) hydrogenated castor oil) physiologic saline and the blood was dissolved by adding distilled water thereto. Thus, the remaining amount of flufenamic acid was analyzed and the amount of flufenamic acid absorbed into the erythrocite cells was determined. The results are also shown in FIG. 3.

As is clear from the results shown in FIG. 3, both the amount of the vesicles adsorbed into the erythrocyte cells and the amount of the flufenamic acid absorbed into (or encapusulated in) the vesicles increased when a positive charge was given to the vesicle particles by including distearyl dimethyl ammonium salt in the vesicle dispersion.

EXAMPLE 10

A 9 g amount of component A of Example 1, 1 g of component B of Example 1, and 2 g of distearyl dimethyl ammonium chloride (i.e., component C) were weighed in a 100 ml beaker and were thoroughly mixed together in the beaker at room temperature. Then, 1 g of hyaluronic acid and 87.0 g of purified water were added to the resultant mixture and were thoroughly mixed together to form a humectant in the form of a uniform translucent milky vesicle dispersion having fluidity. The particle diameters of the vesicles were within 0.1 to 5 $\mu$m.

EXAMPLE 11

A 9 g amount of the component A of Example 1, 1 g of the component B of Example 1, and 0.2 g of benzethonium chloride (i.e., Component C) were thoroughly mixed in a 100 ml beaker as in Example 1. To the resultant mixture, 0.1 g of aloe extracts and 89.7 g of purified water were added and the resultant mixture was thoroughly mixed at a room temperature to form a humectant in the form of a uniform translucent milky vesicle dispersion having fluidity. The particle diameters of the vesicles were within 0.1 to 5 μm.

EXAMPLE 12 to 14

Humectants having the compositions listed in Table 4 were prepared in the same manner as in Example 10. The humectants thus prepared were evaluated by the emollient functions thereof as follows:

That is, the left and right forearms were washed with soap and were allowed to dry naturally for 1 hour. Each humectant was applied to the forearms over an area of 10 cm² at a coating coverage of 100 μg/cm². After drying naturally for 5 minutes and 90 minutes, the impedances of the coated skins were determined by using a radio frequency impedance measurement device (IBS model IB352 manufactured by I.B.S. CO., LTD.) under the constant conditions of 20.5° C. and 50% R.H.

The results are shown in Table 4.

As is clear from the results shown in Table 4, the humectant compositions according to the present invention have an excellent emollient function and humidity reserving characteristics. For reference, the impedance of the non-treated surfaces of the forearms after degreasing was 12±5 μV and 16±5 μV after 5 and 90 minutes.

TABLE 4

| Example No. | 12 | 13 | 14 |
| --- | --- | --- | --- |
| Composition | | | |
| P.O.E. (p̄ = 10) hydrogenated castor oil ether | 9 g | 9 g | 9 g |
| Sorbitan trioleate | 1 g | 1 g | 1 g |
| Benzalkonium chloride | 0.2 g | — | 0.2 g |
| Distearyl dimethyl ammonium chloride | — | 0.2 g | — |
| Sodium pyrrolidone carboxylate | 4.5 g | — | — |
| Hyaluronic acid | — | 1 g | — |
| Aloe extracts | — | — | 0.1 g |
| Purified water | 85.3 g | 87.0 g | 89.7 g |
| Impedance (μV) | | | |
| 5 minutes after drying | 35 ± 4 | 32 ± 4 | 37 ± 5 |
| 90 minutes after drying | 36 ± 7 | 32 ± 5 | 36 ± 5 |

EXAMPLE 15

A humectant having the following composition was formulated into a skin cream.

| Ingredient | Amount (part) |
| --- | --- |
| POE (p = 10) hydrogenated castor oil ether | 9 |
| Sorbitan trioleate | 1 |
| Benzethonium chloride | 0.2 |
| Perfume | 0.03 |
| Aloe ECW | 0.1 |
| 1N—NaOH solution | 3 |
| Carbopol 934* | 1 |
| Purified water | 85.67 |

*Carboxyvinyl polymer manufactured by Goodrich Co., Ltd.

The resultant skin cream exhibited an excellent humidity effect.

EXAMPLE 16

A humectant having the following composition was formulated into a milky lotion.

| Ingredient | Amount (part) |
| --- | --- |
| P.O.E. (p̄ = 10) hydrogenated castor oil ether | 9 |
| Sorbitan trioleate | 1 |
| Benzethonium chloride | 0.2 |
| Perfume | 0.03 |
| Aloe extracts | 0.1 |
| 1N—NaOH solution | 0.3 |
| Carbopol 934 | 0.1 |
| Purified water | 89.27 |

The resultant milky lotion exhibited an excellent humidity effect.

EXAMPLE 17

A 9 g amount of the component A of Example 1, 1 g of sorbitan trioleate, and 0.2 g of benzethonium chloride were thoroughly mixed at a room temperature in a 100 ml beaker. To the resultant mixture, 3 g of Citrus unshiu peel extract and 36.8 g of purified water were added, followed by uniform mixing at room temperature. Thus, a bath salt composition was prepared.

The bath salt composition obtained above was a translucent milky vesicle dispersion having fluidity. The particle diameters of the vesicles were 0.1 to 5 μm.

The heat-retention effect of this bath salt composition was evaluated as follows:

Sensors were fixed by a pressure-sensitive tape at positions 2 to 3 cm below the ancon joint of both forearms. The sensors were fixed at positions other than on the veins in such a manner that the tips of the sensors were in light contact with the skin, without undue pressure but sufficient to ensure that they would not move out of position.

Then, a temperature recording device was actuated to measure the skin temperature before dipping and the fixed positions and fixing pressures of the sensors were adjusted so that the difference in the temperatures between both forearms became as small as possible. After the temperatures were stabilized, the sensors were extracted.

The forearms were each dipped into 20 liters bath water at a temperature of 42° C. for 10 minutes. One bath water contained 10 ml of the bath salt composition prepared above, whereas the other was water alone.

Simultaneously with the completion of the dipping, the temperature recording device was actuated. The arms were thoroughly dried with towels and the sensors were again fixed to the forearms, at the same positions as before the dipping, within 2 minutes. Thus, the changes of the skin temperatures with the lapse of time were measured.

The results are shown in Table 5 below.

TABLE 5

| | | Time period after dipping (minutes) | | | | | |
| --- | --- | --- | --- | --- | --- | --- | --- |
| | | 10 | 20 | 40 | 60 | 90 | 120 |
| Skin Temp. (°C.) | Bath salt composition bath | 34.9 | 34.4 | 33.9 | 33.2 | 32.9 | 32.8 |
| | Water bath | 34.3 | 33.7 | 32.8 | 32.0 | 31.2 | 30.5 |

EXAMPLE 18

A 9 g amount of the component A of Example 1, 1 g of the component B of Example 1, and 2 g of distearyl dimethyl ammonium chloride were thoroughly mixed at a room temperature in a 100 ml beaker. To the resultant mixture, 1 g of hinoki oil and 37 g of purified water were added, followed by uniform mixing at room temperature. Thus, a bath salt composition was prepared.

The bath salt composition obtained above was a translucent milky vesicle dispersion having fluidity The particle diameters of the vesicles were within 0.1 to 5 μm. The heat-retention effect of the bath salt composition was determined in the same manner as in Example 17. The results are shown in Table 6.

TABLE 6

| | | Time period after dipping (minutes) | | | | | |
|---|---|---|---|---|---|---|---|
| | | 10 | 20 | 40 | 60 | 90 | 120 |
| Skin Temp. (°C.) | Bath salt composition bath | 33.7 | 33.1 | 32.5 | 32.0 | 31.7 | 31.6 |
| | Water bath | 33.4 | 32.8 | 32.1 | 31.6 | 30.9 | 30.2 |

EXAMPLE 19

A liquid bath composition having the following composition was prepared by using the bath salt composition prepared in Example 17.

| Ingredient | Amount (g) |
|---|---|
| Bath salt composition of Example 17 | 9.8 |
| Isopropylmethylphenol | 0.2 |
| uranine | 0.3 |
| Perfume | 1.5 |

The liquid bath compositions thus obtained was confirmed to be very effective in use since, as expected, the active component in the bath water was selectively adsorbed and retained on the skin surface.

EXAMPLE 20

A liquid bath composition having the following composition was prepared by using the bath salt composition parepared in Example 18.

| Ingredient | Amount (g) |
|---|---|
| Bath salt composition of Example 18 | 20 |
| Sodium sulfate | 89 |
| Sodium bicarbonate | 106 |
| uranine | 0.4 |
| Perfume | 3 |
| Carboxymethyl cellulose | 1.6 |

The liquid bath composition thus obtained was confirmed to be very effective in use since, as expected, the active component in the bath water was selectively adsorbed and retained on the skin surface.

EXAMPLE 21

A 9 g amount of polyoxyethylene hydrogenated castor oil (E.O.=10 mole on the average), 1 g of sorbitantrioleate, and 0.2 g of benzethonium chloride were mixed, and then 0.1 g of naphazoline hydrochloride, 0.1 g of Dibucaine hydrochloride, 0.2 g of chlorphenylamine maleate, and 0.1 g of allantoin were added as active components to the mixture. Thereafter, 10 g of ethanol and water in such an amount that the total amount of the mixture becomes 100 ml were added to prepare a topical liniment composition.

The composition thus obtained was diluted 50 times with water and 8.0 ml of the diluted composition was charged in a test tube. 0.1 g of keratin powder was added thereto and the test tube was shaken for 2 minutes. The test tube was then subjected to a centrifugal separation for 5 minutes at 3000 r.p.m., and the contents of the active components in the supernatant liquid were determined.

Then, 8 ml of tap water was added to the keratin powder layer and agitated for 2 hours. The resultant mixture was again centrifugally separated, and the contents of the active components in the supernatant liquid were determined. The above-mentioned water washing and centrifugal separation were repeated three times and the retention amounts of the active components adsorbed onto the keratin powder were calculated from the contents of the active components in the supernatant liquid for each time.

On the other hand, as a control, 0.2 g of benzothonium chloride, 0.1 g of naphazolin hydrochloride, 0.1 g of Dibucaine hydrochloride, 0.2 g of chlorphenylamine maleate, 0.1 g of allantoin, and 10 g of ethanol were mixed. The mixture was diluted with water to 100 ml to prepare a control solution. The retention amount of the active components absorbed onto keratin powder was determined in the same manner as mentioned above.

The absorbed amount of each component in the sample compositions for each time is shown in Table 7.

TABLE 7

| | Adsorpability* Washing time | | | |
|---|---|---|---|---|
| Active component | 0 | 1 | 2 | 3 |
| Naphazoline hydrochloride | 2 | 2.5 | 3 | 3 |
| hydrochloride | 2 | 2.5 | 3 | 3 |
| Chlorphenylamine | 2 | 2.5 | 3 | 3 |
| maleate | 3 | 3.3 | 4 | 5 |

*Times of the adsorbed amount of the composition against that of the control solution.

As is clear from the results shown in Table 7, the adsorbability and retentionability of the present composition in the skin are extremely high.

EXAMPLE 22

A 9 g amount of polyoxyethylene hydrogenated castor oil (E.O.=10 mole on average), 1 g of sorbitantrioleate, and 0.2 g of cetylpyridinium chloride were mixed, and then 0.5 g of dephenhydramine hydrochloride, 0.1 g of lidocaine hydrochloride, and 1.0 g of aloe extract were added as active components. The resultant mixture was diluted with water to 100 ml. Thus, a topical liniment composition was prepared.

Ten Wister male rats each having a body weight of about 150 g were treated by cutting the back skin to a length of 4 cm. The wound was closed with forceps and the above-prepared composition was periodically applied each time in an amount of above 2 ml twice a day for 7 days to evaluate the therapeutic effect of the composition. On the eighth day, the back skin was peeled off and the tensile strength of the peeled portion was measured by an Instrone tensile test machine.

Comparisons were conducted with samples having no-treatment (i.e., Control) and where an aqueous solution only containing 0.2 g of cetylpyridinium chloride, 0.5 g of diphenhydramine hydrochloride, 0.1 g of lidocaine hydrochloride, and 1.0 g of aloe extract was applied (i.e., Comparative Example), when the above-mentioned evaluation tests were carried out.

The results are shown in Table 8.

TABLE 8

| Sample | Number of Rats | Tensile Strength (g/cm) |
|---|---|---|
| Control | 10 | 466 ± 60.5 |
| Present Invention | 10 | 570 ± 83.3 |
| Comparative Example | 10 | 520 ± 82.8 |

As is clear from the results shown in Table 8, the therapeutic effects were accelerated when the active components were applied.

Furthermore, the same evaluation tests were carried out in the same manner as mentioned above, except that the applied portions were washed with water 1 minute after the application.

The results are shown in Table 9.

TABLE 9

| Sample | Number of Rats | Tensile Strength (g/cm) |
|---|---|---|
| Control | 10 | 466 ± 60.5 |
| Present Invention | 10 | 550 ± 72.3 |
| Comparative Example | 10 | 473 ± 66.0 |

As is clear from the results shown in Table 9, since the present composition has high retentionability in the skin, the therapeutic effect was excellent, when compared with the comparative composition, even when water washing was carried out.

EXAMPLE 23

A 9 g amount of polyoxyethylene (E.O.=10 mole on average) hydrogenated castor oil, 1 g of sorbitan trioleate, 0.2 g of benzethonium chloride, and 1.0 g of Rosemary extract were mixed together and small amounts of perfume and saccharin were added thereto. Then, 10 g of ethanol was added and water was added to the mixture in such an amount that the total volume of the mixture was 100 ml. Thus, a mouth washing composition was prepared.

The mouth washing composition thus obtained was diluted with 0.1M phosphoric buffer, having a pH of 9, to 40 times. This composition was evaluated by using a panel of 4 persons having a relatively large amount of mercaptan as follows.

40 ml of the above-prepared diluted composition was held for 15 seconds in the mouth of the person in the panel, and then was ejected from the mouth. This process was repeated twice. Thereafter, the mouth was rinsed with tap water. The relative intensity of foul breath before and after washing the mouth was epidemically determined by a panel of three persons according to the following criteria.

| Score | Composition |
|---|---|
| +2 | Very strong foul breath when compared with before washing |
| +1 | Strong foul breath when compared with before washing |
| +0.5 | Slightly strong foul breath when compared with before washing |
| 0 | No substantial difference when compared with before washing |
| −0.5 | Slightly weakened foul breath when compared with before washing |
| −1 | Weak foul breath when compared with before washing |
| −2 | Very weak foul breath when compared with before washing |

Figure 4:
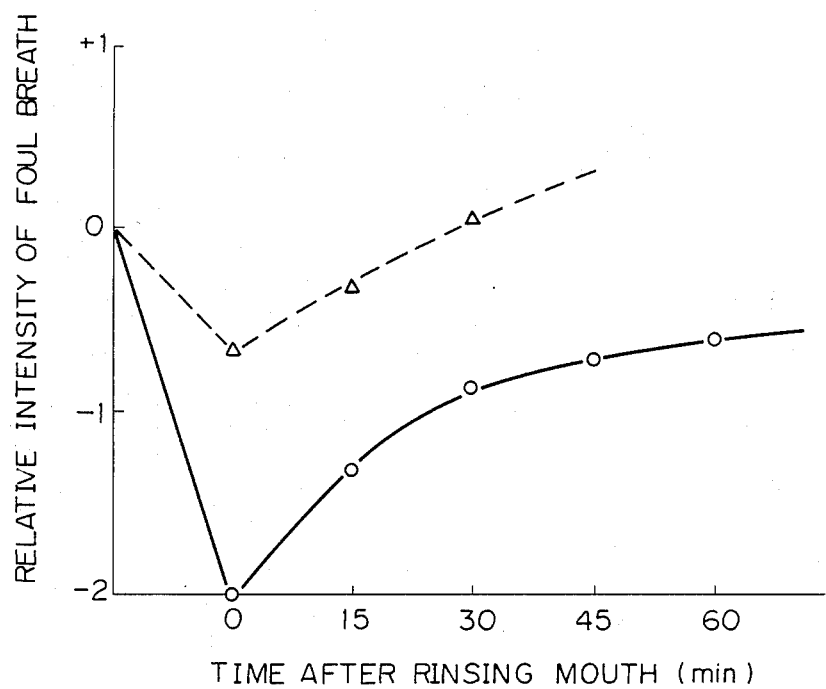
FIG. 4 is a graph illustrating the correlation between the relative intensity of foul breath over a period after rinsing a mouth.

The results are shown as a solid line curve in FIG. 4, which illustrates the relative intensity of the foul breath with the lapse of time.

As a Comparative Example, a mouth washing composition was prepared in the same manner as mentioned above, except that the polyoxyethylene hydrogenated castor oil and sorbitan trioleate were not included. The comparative composition thus prepared was evaluated in the same manner as mentioned above. The results are also shown as a dotted line curve in FIG. 4.

As is clear from the results shown in FIG. 4, the present composition has a large effect on suppressing foul breath for a long period of time, when compared to the comparative composition.

EXAMPLE 24

Various components listed in Table 10 were weighed and mixed together, in the amounts listed in Table 10 in a 100 ml beaker. Then, water was added to the resultant mixture in the amount listed in Table 10. The mixture was thoroughly mixed by means of a magnetic stirrer so as to form a uniform mixture. The sample composition Nos. 1 and 2 in Table 10 provide a translucent white milky aqueous vesicle dispersion having fluidity or flowability. However, no vesicle dispersion was obtained in a sample composition No. 3.

The formation of the vesicles in the sample dispersion Nos. 1 and 2 was confirmed by an electron microscope, and the sizes of the vesicle particles were 0.1 to 5 μm in each sample.

TABLE 10

| Ingredients | Sample No. 1 | Sample No. 2 | Sample No. 3 |
|---|---|---|---|
| Flufenamic acid | 0.1 g | 0.1 g | 0.1 g |
| Polyoxyethylene hydrogenated castor oil ether ($\bar{p}$ = 10) | 12 g | 12 g | — |
| Sorbitan trioleate | 1.2 g | 1.2 g | — |
| Benzethonium chloride | 0.3 g | — | — |
| Ethanol | 20 g | 20 g | 20 g |
| Water | Balance | Balance | Balance |
| Total | 100 g | 100 g | 100 g |

The same dispersions obtained above were diluted with 20 time amount of physiological saline. The diluted sample dispersion was evaluated as follows. Mucosa from the cheek pouch of Golden Hamsters having an area of 4 cm$^2$ was peeled off. After washing with physiological saline, the peeled off strip of the cheek pouch was dipped, as a model of human body skin area, in 8 ml of the test dispersion (the amount of flufenamic acid in the test dispersion is defined as A mg), followed by shaking at a temperature of 40° C for 5 hours. The amount (i.e., B mg) of the flufenamic acid in the supernatant after shaking was determined.

The cheek pouch mucosa was again dipped in 4 ml of physiologic saline and was shaken at a temperature of 40° C for 5 minutes. This operation was repeated 5 times in total. The amounts (C mg) of the flufenamic acid in the supernatant after 3 time and 5 time operations were determined.

The amount of the flufenamic acid adsorbed and retained in the cheek pouch mucosa was calculated as follows:

Adsorption and retention amount=A−B−C

The ratio of the amount of the flufenamic acid of the sample No. 1 or 2 to that of the sample No. 3 (control) was determined in 0, 3, and 5 times of the washing. The results are shown in Table 11.

TABLE 11

| Sample No. | Adsorbability* | | |
|---|---|---|---|
| | 0 | 3 | 5 |
| 1 | 5 | 5 | 5 |
| 2 | 3 | 2 | 1.5 |

*Times of the adsorbed amount of the sample composition against that of the control sample (i.e., sample No. 3).

As is clear from the results shown in Table 11, the vesicle dispersion of the sample No. 2 had high adsorbability when compared to the sample No. 3 (control), although the active component (i.e., the flufenamic acid) was desorbed by the washing.

The vesicle dispersion of the sample No. 1 had not only high initial adsorbability but also high retentionability (i.e., high adsorbability) after the washing.

EXAMPLE 25

Typical formulations of the compositions according to the present invention are as follows:

| Ingredient | Content (g) |
|---|---|
| (i) Therapeutic Preparation For Suppurative Skin Disease | |
| Benzethonium chloride | 0.2 |
| Sulfamethoxazol | 4 |
| Monoethanolamine | 0.99 |
| Polyoxyethylene hydrogenated castor oil ($\bar{p}$ = 10) | 9 |
| Sorbitan trioleate | 1 |
| Fradiomycin sulfate | 1 |
| Ethanol | 10 |
| Water | Amount to 100 ml in total |
| (ii) External Analgesic And Anti-Inflammatory Preparation | |
| l-menthol | 2 |
| dl-camphor | 2 |
| Thymol | 0.5 |
| Tocopherol acetate | 0.2 |
| Methyl salicylate | 3 |
| Glycol salicylate | 1 |
| Benzalkonium chloride | 0.1 |
| Capusicum extract | 0.25 |
| Polyoxyethylene hydrogenated castor oil ($\bar{p}$ = 10) | 9 |
| Sorbitan trioleate | 1 |
| Ethanol | 30 |
| Water | Amount to 100 ml in total |
| (iii) Therapeutic Preparation For Parasitic Skin Disease | |
| Clotrimazole | 1 |
| Benzalkonium chloride | 0.2 |
| Polyoxyethylene hydrogenated castor oil ($\bar{p}$ = 10) | 9 |
| Sorbitan trioleate | 1 |
| Ethanol | 1 |
| Water | Amount to 100 ml in total |
| (iv) Hair Treatment Composition | |
| Estradiol benzoate | 0.001 |
| Hydrocortisone | 0.0016 |
| Capronium chloride | 0.5 |
| Polyoxyethylene hydrogenated castor oil ($\bar{p}$ = 10) | 9 |
| Sorbitan trioleate | 1 |
| Benzalkonium chloride | 0.02 |
| Ethanol | 10 |
| Water | Amount to 100 ml in total |
| (v) Bacteriocide and Disinfectant | |
| Benzethonium chloride | 0.2 |
| Lyzozyme chloride | 0.5 |
| Polyoxyethylene hydrogenated castor oil ($\bar{p}$ = 10) | 9 |
| Sorbitan trioleate | 1 |
| Ethanol | 10 |
| Water | Amount to 100 ml in total |
| (vi) Gargle Composition | |
| Benzethonium chloride | 0.2 |
| Sodium gualenate | 0.3 |
| l-Menthol | 0.6 |
| Thymol | 0.1 |
| α-Borneol | 0.1 |
| Ascorbic acid | 0.2 |
| Chlorophenylamine maleate | 0.2 |
| Methyl ephedrine hydrochloride | 0.2 |
| Polyoxyethylene hydrogenated castor oil ($\bar{p}$ = 10) | 9 |
| Sorbitan trioleate | 1 |
| Ethanol | 10 |
| Water | Amount to 100 ml in total |

This composition is diluted 20 times when used.

| Ingredient | Content (g) |
|---|---|
| (vii) Pharynx And Nasal Liniment | |
| Naphazoline nitrate | 0.05 |
| Dipotassium glycyrrhizinate | 0.3 |
| Lysozyme chloride | 0.5 |
| Proccaine hydrochloride | 0.1 |
| Benzalkonium chloride | 0.02 |
| Polyoxyethylene hydrogenated castor oil ($\bar{p}$ = 10) | 9 |
| Sorbitan trioleate | 1 |
| Ethanol | 10 |
| Water | Amount to 100 ml in total |
| (viii) Eye drops A | |
| Benzalkonium chloride | 0.01 |
| Flavine adenine dinucleotide | 0.02 |
| Sulfamethoxazol | 4 |
| Monoethanol amine | 0.99 |
| Neostigmin methylsulfate | 0.002 |
| Polyoxyethylene hydrogenated castor oil ($\bar{p}$ = 10) | 3 |
| Sorbitan trioleate | 0.3 |
| Water | Amount to 100 ml in total |
| (ix) Eye drops B | |
| Benzalkonium chloride | 0.01 |
| Fluorometholone | 0.1 |
| Polyoxyethylene hydrogenated castor oil ($\bar{p}$ = 10) | 3 |
| Sorbitan trioleate | 0.3 |
| Boric acid | 1.5 |
| Water | Amount to 100 ml in total |
| (x) Eye drops C | |
| Benzalkonium chloride | 0.01 |
| Erythromycin lactobionate | 0.5 |
| Sodiumcholine methanesulfonate | 0.5 |
| Polyoxyethylene hydrogenated castor oil ($\bar{p}$ = 10) | 3 |
| Sorbitan trioleate | 0.3 |
| Water | Amount to 100 ml in total |
| (xi) Gastrointestinal Drug | |
| Benzalkonium chloride | 0.05 |
| Methylmethionine sulfonium chloride | 0.5 |
| Glycyrrhizin | 0.7 |
| Sodium copper chlorophyll | 0.1 |
| Polyoxyethylene hydrogenated | 9 |

| Ingredient | Content (g) |
| --- | --- |
| castor oil ($\bar{p}$ = 10) | |
| Sorbitan trioleate | 1 |
| Water | Amount to 100 ml in total |

The above-mentioned compositions (i) to (xi) exhibited no vesicle separation and, therefore, had excellent stability.

We claim:

1. An aqueous vesicle dispersion having a surface charge the vesicle dispersion comprising, in an aqueous dispersion medium:
   (A) 100 parts by weight of a nonionic surfactant which is at least one ethoxylate having an average ethylene oxide addition mole number of 7 to 20 selected from the group consisting of polyoxyethylene castor oil ethers and polyoxyethylene hydrogenated caster oil ethers,
   (B) 3 to 30 parts by weight of a nonionic surfactant which is at least one sorbitan polyester of long-chain fatty acid, having a fatty acid residue with 14 to 18 carbon atoms and a degree of esterification of 2.5 to 3.5, and
   (C) at least one ionic surfactant in such an amount that the formation of the vesicle particles from the components (A) and (B) is not adversely affected, the components (A), (B), and (C) being dispersed in an aqueous medium in such a manner that the components (A) and (B) form vesicle particles in the aqueous medium and the component (C) provides a surface charge on the vesicle particles.

2. A vesicle dispersion as claimed in claim 1, wherein said ethoxylate has an average ethylene oxide addition mole number of 7 to 20.

3. A vesicle dispersion as claimed in claim 1, wherein said sorbitan polyester is at least one member selected from the group consisting of sorbitan polyesters of long-chain fatty acids having the fatty acid residues with 14 to 18 carbon atoms.

4. A vesicle dispersion as claimed in claim 1, wherein said ionic surfactant is at least one member selected from the group consisting of dialkyl type quaternary ammonium salts having two alkyl groups with 14 to 22 carbon atoms.

5. A vesicle dispersion as claimed in claim 1, wherein said ionic surfactant is at least one member selected from the group consisting of monoalkyl type quaternary ammonium salts having an alkyl group with 14 to 22 carbon atoms, alkyl dimethyl benzyl ammonium salts having an alkyl group with 8 to 12 carbon atoms, and alkyl pyridinium salts having an alkyl group with 12 to 22 carbon atoms and the amount of the ionic surfactant is 10% by weight or less of the total amount of the surfactants in the dispersion.

6. A vesicle dispersion as claimed in claim 1, wherein said ionic surfactant is at least one member selected from the group consisting of quaternary ammonium salts having hydroxyl group, ether linkage, and amide linkage and the amount of the ionic surfactant is 10% by weight or less of the total amount of the surfactants in the dispersion.

7. A vesicle dispersion as claimed in claim 1, wherein said ionic surfactant is at least one member selected from the group consisting of long-chain alkylamines having 14 to 22 carbon atoms and their salts, di(long-chain alkyl) amine having 14 to 22 carbon atoms and their salts, the alkylene oxide addition products of long-chain alkylamines having 14 to 22 carbon atoms and their salts, and 2-alkyl substituted imidazolinium salts having an alkyl group with 14 to 22 carbon atoms and the amount of the ionic surfactant is 10% by weight or less of the total amount of the surfactants in the dispersion.

8. A vesicle dispersion as claimed in claim 1, wherein said ionic surfactant is at least one biguanide compound and the amount of the ionic surfactant is 5% by weight or less of the total amount of the surfactants in the dispersion.

9. A vesicle dispersion as claimed in claim 8, wherein said bisbiguanide compound is chlorhexidine or its salt.

10. A vesicle dispersion as claimed in claim 1, wherein said ionic surfactant is at least one phospholipid and the amount of the ionic surfactant is 50% by weight or less of the total amount of the surfactants in the dispersion.

11. A vesicle dispersion as claimed in claim 1, wherein said ionic surfactant is at least one member selected from the group consisting of phosphoric mono esters and diesters of long-chain alcohols having the alcohol residues with 14 to 22 carbon atoms and their salts, phosphoric monoesters and diesters of alkylene oxide addition products of long-chain alcohols having the alcohol residues with 14 to 22 carbon atoms and their salts, alkylsulfates having 14 to 22 carbon atoms, polyoxyethylene alkyl ether sulfates of alcohols having the alcohol residues with 14 to 22 carbon atoms, alkanesulfonates having 14 to 22 carbon atoms, and olefin sulfonates having 14 to 22 carbon atoms and the amount of the ionic surfactant is 1% by weight or less of the total amount of the surfactants in the dispersion.

12. A vesicle dispersion as claimed in claim 1, wherein said ionic surfactant is at least one anionic phospholipid and the amount of the ionic surfactant is 50% by weight or less of the total amount of the surfactants.

13. The aqueous vesicle dispersion of claim 1, wherein the amount of components (A), (B), and (C), in total, is between 0.1% and 50% by weight of the total weight of the aqueous vesicle dispersion.

* * * * *